United States Patent
Kanowitz

(10) Patent No.: US 8,001,969 B2
(45) Date of Patent: Aug. 23, 2011

(54) COMPLETE AIRWAY STABILIZATION SYSTEM AND METHOD

(75) Inventor: Arthur Kanowitz, Littleton, CO (US)

(73) Assignee: Securisyn Medical, LLC, Littleton, CO (US)

( * ) Notice: Subject to any disclaimer, the term of this patent is extended or adjusted under 35 U.S.C. 154(b) by 1078 days.

(21) Appl. No.: 11/346,686

(22) Filed: Feb. 3, 2006

(65) Prior Publication Data

US 2006/0174893 A1    Aug. 10, 2006

Related U.S. Application Data

(60) Provisional application No. 60/593,702, filed on Feb. 7, 2005.

(51) Int. Cl.
*A61M 16/00* (2006.01)
*A62B 9/06* (2006.01)

(52) U.S. Cl. .............. 128/207.14; 128/207.17

(58) Field of Classification Search ............. 128/207.14, 128/200.26, 207.15, 207.16, 207.17, 207.18
See application file for complete search history.

(56) References Cited

U.S. PATENT DOCUMENTS

| | | | |
|---|---|---|---|
| 3,137,299 A | | 6/1964 | Tabor |
| 3,288,136 A | | 11/1966 | Lund |
| 3,946,742 A | | 3/1976 | Eross |
| 3,987,798 A | * | 10/1976 | McGinnis ........... 128/207.17 |
| 4,056,104 A | | 11/1977 | Jaffe |
| 4,269,184 A | | 5/1981 | Montgomery |
| 4,324,235 A | | 4/1982 | Beran |
| 4,341,210 A | | 7/1982 | Elam |
| 4,501,273 A | | 2/1985 | McGinnis |
| 4,520,813 A | | 6/1985 | Young |
| 4,527,559 A | | 7/1985 | Roxburg et al. |
| 4,530,354 A | | 7/1985 | Froilan |
| 4,548,200 A | | 10/1985 | Wapner |
| 4,589,410 A | | 5/1986 | Miller |
| 4,622,034 A | | 11/1986 | Shattuck |
| 4,658,814 A | | 4/1987 | Anderson |
| 4,683,882 A | | 8/1987 | Laird |
| 4,744,358 A | | 5/1988 | McGinnis |
| 4,774,943 A | | 10/1988 | Yu |
| 4,774,944 A | | 10/1988 | Mischinski |
| 4,832,019 A | | 5/1989 | Weinstein |

(Continued)

FOREIGN PATENT DOCUMENTS

DE    19533615    4/1997

(Continued)

OTHER PUBLICATIONS

International Search Report, PCT/US2006/004253, Jul. 4, 2006.

(Continued)

*Primary Examiner* — Justine Yu
*Assistant Examiner* — Colin W Stuart
(74) *Attorney, Agent, or Firm* — Glenn H. Lenzen; Husch Blackwell LLP

(57) ABSTRACT

An endotracheal airway is established using an endotracheal tube having an exterior retention structure defined by a series of longitudinally spaced recesses separated by projections. A variably-sized orifice in a faceplate constricts within a recess and contacts the projections to create a barrier against movement of the endotracheal tube. The faceplate is retained on the mouth by connection to a stabilization collar which surrounds the neck of the patient to restrain against flexion and extension which could reposition the endotracheal tube from its desired position.

12 Claims, 14 Drawing Sheets

U.S. PATENT DOCUMENTS

| | | | |
|---|---|---|---|
| 4,869,718 A | | 9/1989 | Brader |
| 4,886,059 A | | 12/1989 | Weber |
| 5,009,227 A | | 4/1991 | Nieuwstad |
| 5,069,206 A | * | 12/1991 | Crosbie ............... 128/207.17 |
| 5,076,269 A | | 12/1991 | Austin |
| 5,251,616 A | | 10/1993 | Desch |
| 5,305,742 A | | 4/1994 | Styers et al. |
| 5,311,864 A | | 5/1994 | Huerta |
| 5,320,097 A | | 6/1994 | Clemens et al. |
| 5,341,802 A | * | 8/1994 | Calebaugh ............... 128/207.17 |
| 5,345,931 A | | 9/1994 | Battaglia, Jr. |
| 5,353,787 A | | 10/1994 | Price |
| 5,368,024 A | | 11/1994 | Jones |
| 5,382,239 A | | 1/1995 | Orr et al. |
| 5,398,679 A | | 3/1995 | Freed |
| 5,402,776 A | | 4/1995 | Islava |
| 5,419,319 A | | 5/1995 | Werner |
| 5,429,127 A | | 7/1995 | Kolobow |
| 5,437,273 A | | 8/1995 | Bates et al. |
| 5,443,064 A | | 8/1995 | Theis et al. |
| 5,447,152 A | | 9/1995 | Kohsai et al. |
| 5,448,985 A | | 9/1995 | Byrd |
| 5,490,504 A | | 2/1996 | Vrona et al. |
| 5,513,633 A | | 5/1996 | Islava |
| 5,551,421 A | | 9/1996 | Noureldin et al. |
| 5,555,881 A | | 9/1996 | Rogers et al. |
| 5,558,090 A | | 9/1996 | James |
| 5,623,924 A | | 4/1997 | Lindenman et al. |
| 5,638,814 A | | 6/1997 | Byrd |
| 5,653,232 A | | 8/1997 | Rogers et al. |
| 5,683,458 A | | 11/1997 | Urken |
| 5,699,787 A | | 12/1997 | Thompson |
| 5,795,315 A | | 8/1998 | Traut et al. |
| 5,803,079 A | | 9/1998 | Rogers et al. |
| 5,806,516 A | | 9/1998 | Beattie |
| 5,829,430 A | | 11/1998 | Islava |
| 5,862,801 A | | 1/1999 | Wells |
| 5,868,132 A | | 2/1999 | Winthrop et al. |
| 5,894,840 A | | 4/1999 | King |
| 5,928,198 A | * | 7/1999 | Lester ............... 604/164.04 |
| 5,934,276 A | | 8/1999 | Fabro et al. |
| 5,941,246 A | | 8/1999 | Roopchand |
| 5,996,581 A | | 12/1999 | Duch |
| 6,010,484 A | | 1/2000 | McCormick et al. |
| 6,029,668 A | | 2/2000 | Freed |
| 6,050,263 A | | 4/2000 | Choksi et al. |
| 6,053,166 A | | 4/2000 | Gomez |
| 6,067,985 A | | 5/2000 | Islava |
| 6,090,058 A | | 7/2000 | Traut et al. |
| 6,105,573 A | * | 8/2000 | Delaplane et al. ....... 128/200.26 |
| 6,105,577 A | | 8/2000 | Varner |
| 6,432,085 B1 | | 8/2002 | Stellon et al. |
| 6,526,978 B2 | | 3/2003 | Dominguez |
| 6,568,393 B2 | | 5/2003 | Christopher |
| 6,606,991 B2 | | 8/2003 | Chou |
| 6,634,359 B1 | | 10/2003 | Rudy, Jr. et al. |
| 6,663,581 B1 | | 12/2003 | Calabrese |
| 6,668,832 B2 | | 12/2003 | Hipolito et al. |
| 6,726,643 B1 | | 4/2004 | Martin |
| 6,761,171 B2 | | 7/2004 | Toti et al. |
| 6,763,831 B2 | | 7/2004 | Sniadach |

FOREIGN PATENT DOCUMENTS

| | | |
|---|---|---|
| DE | 19636050 | 3/1998 |
| EP | 0982045 | 3/2000 |
| GB | 2165157 A | 4/1986 |
| GB | 2340757 | 3/2000 |
| WO | WO 80/02645 | 12/1980 |
| WO | 9933507 | 7/1999 |

OTHER PUBLICATIONS

Dow Corning Corporation, *SILASTIC® Endotracheal Tube*, Oct. 1971, 2 pages.

* cited by examiner

COMPLETE AIRWAY STABILIZATION SYSTEM AND METHOD

CROSS REFERENCE TO RELATED APPLICATION

This application claims the benefit of U.S. Provisional Application US60/593,702, filed Feb. 7, 2005.

FIELD OF THE INVENTION

This invention relates to endotracheal intubation, and more particularly to a new and improved system and method which make use of an endotracheal tube, a faceplate, and a head and neck stabilization collar, all of which cooperatively interact to provide improved stabilization and maintenance of an airway into the lungs for respiration.

BACKGROUND OF THE INVENTION

Endotracheal intubation is a medical procedure used to place an endotracheal tube (artificial airway) into a patient's airway. The endotracheal tube becomes necessary when a patient is unable to maintain a patent airway on their own due to unconsciousness, trauma, disease, drugs or anesthesia. An endotracheal tube may also become necessary when a patient's own respiratory drive is either ineffective or absent due to trauma, disease, drugs or anesthesia, thus requiring mechanical ventilation through the endotracheal tube.

Endotracheal intubation is accomplished by inserting an endotracheal tube into the mouth, through the throat and larynx or voice box, and into the trachea or air passageway which then branches into the bronchial tubes that connect with the lungs. Positioning the endotracheal tube in this manner prevents these natural passageways from collapsing or occluding, thereby permitting respiration air to flow into and out of the lungs. Because a cardiopulmonary arrest may be sustained anywhere, endotracheal tubes must be inserted in out-of-hospital emergency settings by paramedic emergency medical service personnel as well as in hospital settings by emergency department, operating room, and critical care personnel.

It is very important that the endotracheal tube be positioned correctly and maintained in the correct position. If the tube moves out of its proper position in the trachea and into either the right or left mainstem bronchial tube, only one lung will be ventilated. The failure to ventilate the other lung can lead to multiple severe pulmonary difficulties. If the tube moves completely out of its proper position in the trachea and into the esophagus, the patient will become hypoxic due to the lack of ventilation to the lungs, typically resulting in life-threatening brain injury within several minutes.

Even after the endotracheal tube has been positioned correctly, subsequent movement of the patient can lead to inadvertent mal-positioning of the endotracheal tube. Flexion or extension of the patient's neck can apply either a pulling or pushing force on the endotracheal tube, causing the endotracheal tube to move from the trachea into the esophagus or to extend from the trachea into one of the mainstem bronchial tubes, respectively. Such unintentional movement is not uncommon, because the patient frequently needs to be moved, particularly when the patient is moved from an out-of-hospital setting to an emergency department of a hospital. It is sometimes necessary to transfer an intubated patient from one hospital to another hospital, or to move the intubated patient from one area of the hospital to another area in the same hospital. Even repositioning an intubated patient in a hospital bed may cause unintentional movement of the endotracheal tube.

Inadvertent movement of the endotracheal tube may also occur as a result of moving external ventilation equipment, such as a conventional mechanical ventilator or bag valve mask, which is connected to the external end of the endotracheal tube. External ventilation equipment is connected to the endotracheal tube under circumstances where the patient can no longer naturally achieve respiration. Typically, the external ventilation equipment is connected to the external end of the endotracheal tube by an air conduit to establish air flow to and from the lungs through the endotracheal tube. Inadvertent pulling on, or other excessive movement of the air conduit, may transfer movement to the endotracheal tube, thereby moving the endotracheal tube and possibly inadvertently repositioning it from its proper position.

The problem of maintaining the endotracheal tube in the correct position has been recognized and addressed by various prior art devices. Such devices have attempted to secure the endotracheal tube in the proper position and to prevent inadvertent and unintended movement of it. The most common approach for securing the endotracheal tube is tying umbilical tape, which is formed from a cloth material, around the patient's neck and then wrapping and tying the umbilical tape around the smooth outside surface of the endotracheal tube itself. Arranged in this manner, the umbilical tape is intended to anchor the endotracheal tube to the corner of the patient's mouth and prevent its unintentional movement. While the use of the umbilical tape in this manner provides some benefit, the restraint available from the umbilical tape usually diminishes because the tape becomes covered and saturated with blood, saliva, or other bodily fluids, thereby diminishing the frictional restraint of the tape around the endotracheal tube. Consequently, the endotracheal tube is usually able to move from the proper position, even when wrapped with the umbilical tape.

Various auxiliary mechanical securing devices have also been employed to attempt to maintain the endotracheal tube. Many of these auxiliary mechanical devices include some type of faceplate which is attached to the patient's face, usually with one or more straps that extend around the back of the patient's head or neck. The faceplate includes some type of mechanical contact device that grips the endotracheal tube. Typical mechanical contact devices include thumb screws, clamps, adhesives, locking teeth, and straps.

One of the problems with many of these auxiliary mechanical contact devices is that the gripping action becomes less effective when the endotracheal tube becomes wet from bodily fluids, thereby substantially diminishing or eliminating any restraint provided by these devices. To maintain an effective restraint, it is frequently necessary to increase the amount of clamping force applied on the endotracheal tube. Increasing the amount of clamping force to an effective level usually pinches the tube to the point where of the inner tube diameter and hence air passageway is significantly restricted. Restricting the cross-sectional size of the air passageway decreases the ventilatory efficiency of the tube, thereby decreasing the respiratory airflow. The restriction of the cross-sectional size of the air passageway creates resistance to both inspiratory airflow and expiratory airflow. The resistance to inspiration creates either a decreased volume of airflow at a given pressure or an increased pressure to maintain a given airflow. Insufficient airflow can lead to hypoxemia, and increased pressure can lead to barotrauma in the lungs. Resistance to expiratory airflow leads to multiple adverse effects within the lungs. Impairing a patient's ventilations may result in serious medical effects, particularly with patients whose functions are already compromised.

The problem of preventing flexion or extension of the head and neck during endotracheal intubation has been addressed by placing a conventional cervical collar around the neck of the patient. The cervical collar used for this purpose is the typical type used to restrain head and neck movement under circumstances of injury or potential injury to the neck or spinal column. In other words, the cervical collar used during endotracheal intubation is intended to be used for different purpose.

SUMMARY OF THE INVENTION

The present invention provides a multi-pronged approach to preventing malpositioning of the endotracheal tube and maintaining the endotracheal tube in the correct and proper position for intubation. A new and improved endotracheal tube and faceplate interact with one another to prevent relative movement, even under conditions where bodily fluids cover the tracheal tube. A new and improved stabilization collar fits around the neck and prevents unintentional movement of the head and neck while simultaneously interacting with the faceplate to assure that the endotracheal tube is maintained in the proper position while the head and neck are stabilized against unintentional movement. In contrast to known prior art arrangements, the present invention provides a complete system and method for positioning, maintaining and stabilizing the endotracheal tube.

One form of the invention relates to apparatus for establishing an endotracheal airway in a patient with an endotracheal tube. The endotracheal tube has a continuous sidewall which defines a hollow conduit through which the airway is established. The endotracheal tube has a length which extends from a distal end to a proximal end, to allow the distal end to be positioned in the trachea of the patient and the proximal end to be positioned external of the mouth of the patient. A retention structure is located on the exterior of the sidewall between the proximal and distal ends. The retention structure extends along a predetermined length of the sidewall at a predetermined position relative to the distal end to locate at least a portion of the retention structure adjacent to the mouth of the patient when the distal end is positioned in the trachea to establish the airway. The retention structure defines a series of longitudinally spaced recesses separated by a series of longitudinally spaced projections extending along the predetermined length of the sidewall.

In certain forms of the endotracheal tube, the retention structure is integrally formed with the sidewall, each projection comprises an annular flange surrounding the sidewall, each annular flange is fixedly positioned relative to the sidewall, each annular flange is integral with the sidewall, and indications are associated with the recesses to describe the position of each recess relative to the distal end.

In addition to the endotracheal tube, another form of the apparatus includes a faceplate which contacts the face of the patient at the mouth. A variably-sized orifice is formed in the faceplate. The orifice expands in size to accept the endotracheal tube and the projections, and the orifice contracts in size to constrict within a selected recess and contact the projections adjacent to the selected recess and create a barrier which limits longitudinal movement of the endotracheal tube relative to the faceplate at the selected recess.

One form of the faceplate comprises a pair of faceplate sections which overlap with one another and which moveably connect to one another to permit the faceplate sections to move toward and away from one another. Each faceplate section includes a lateral opening of a predetermined configuration. The lateral openings in the two faceplate sections overlap with one another to form the orifice. The size of the orifice expands upon relative movement of the faceplate sections toward one another and constricts upon relative movement of the faceplate sections away from one another, as a result of the predetermined configurations of the lateral openings. The faceplate sections move toward one another a sufficient distance to expand the orifice to accept the endotracheal tube and the projections within the orifice, and the faceplate sections move away from one another a sufficient distance to constrict the orifice within the selected recess and contact the faceplate sections with the projections adjacent to the selected recess and create the barrier which limits longitudinal movement of the endotracheal tube. A fixation structure maintains the faceplate sections moved away from one another to constrict the orifice within the selected recess and to create the barrier which limits longitudinal movement. The fixation structure may include fixation bands which extend away from each of the faceplate sections to hold the faceplate sections in a position moved away from one another and hold the faceplate in position at the mouth of the patient.

In addition to the endotracheal tube and the faceplate, another form of the apparatus includes a stabilization collar which surrounds the neck of the patient to restrain the head and neck against flexion and extension which could reposition the distal end of the endotracheal tube from a desired position to establish the airway. The fixation bands may extend from the faceplate to the stabilization collar to maintain the faceplate in position at the mouth of the patient with the orifice constricted around the selected recess to create the barrier. The stabilization collar may comprise anterior portion and a posterior portion, the anterior portion of the stabilization collar may be adjustable in length between the chest and chin of the patient, and the fixation bands may extend between the faceplate to the posterior portion of the stabilization collar.

Another form of the invention relates to a method of establishing an endotracheal airway in a patient. The method includes extending an elongated endotracheal tube into the mouth and through the throat and larynx of the patient until a distal end of the endotracheal tube extends into the trachea of the patient while a proximal end of the endotracheal tube is located external of the mouth of the patient. The endotracheal tube used in the method has a retention structure which extends along a predetermined distance between the proximal and distal ends to locate at least a portion of the retention structure adjacent to the mouth of the patient when the distal end is positioned in the trachea to establish the airway. The retention structure defines a series of longitudinally spaced recesses separated by a series of longitudinally spaced projections. The method further involves extending the proximal end of the endotracheal tube through an orifice in a faceplate, fixing a faceplate relative to the head of the patient to locate the faceplate at the mouth of the patient, constricting the orifice at a selected recess of the retention structure, and contacting the projections adjacent to the selected recess with the faceplate to create a barrier which limits longitudinal movement of the endotracheal tube relative to the faceplate at the selected recess.

Other forms of the method include using a faceplate which comprises a pair of faceplate sections which overlap with one another and which are connected to move toward and away from one another. Each faceplate also includes a lateral opening of a predetermined configuration which overlaps with the other lateral opening in the other faceplate section to form the orifice. The method further involves expanding the size of the orifice upon relative movement of the faceplate sections toward one another when extending the proximal end of the endotracheal tube through the orifice, and constricting the size of the orifice at the selected recess and creating the barrier which limits longitudinal movement of the endotracheal tube relative to the faceplate at the selected recess upon relative movement of the faceplate sections away from one another. The other forms of the method include maintaining the faceplate sections moved away from one another by fixing the faceplate sections relative to the head of the patient in a position with the faceplate sections moved away from one another, surrounding the neck of the patient with a stabilization collar to restrain the head and neck against flexion and extension which would reposition the distal end of the endotracheal tube from the desired position within the trachea, fixing the faceplate sections to the stabilization collar in a position moved away from one another and to fix the faceplate relative to the mouth, using a stabilization collar which comprises anterior portion and a posterior portion which respectively surround the front and the back of the neck, attaching the anterior and posterior portions to one another to maintain the stabilization collar surrounding the neck of the patient, adjusting the length of the anterior portion between the chest and chin of the patient, and extending fixation bands between the faceplate sections and the posterior portion to maintain the faceplate sections moved away from one another and to fix the faceplate relative to the mouth. In addition, the mouth and oral cavity of the patient may be accessed through the lateral openings while the orifice is constricted within the selected recess and the faceplate sections are maintained in position moved away from one another.

A more complete appreciation of the scope of the present invention and the manner in which it achieves the above-noted and other improvements can be obtained by reference to the following detailed description of presently preferred embodiments taken in connection with the accompanying drawings, which are briefly summarized below, and by reference to the appended claims.

DETAILED DESCRIPTION

Figure 1:
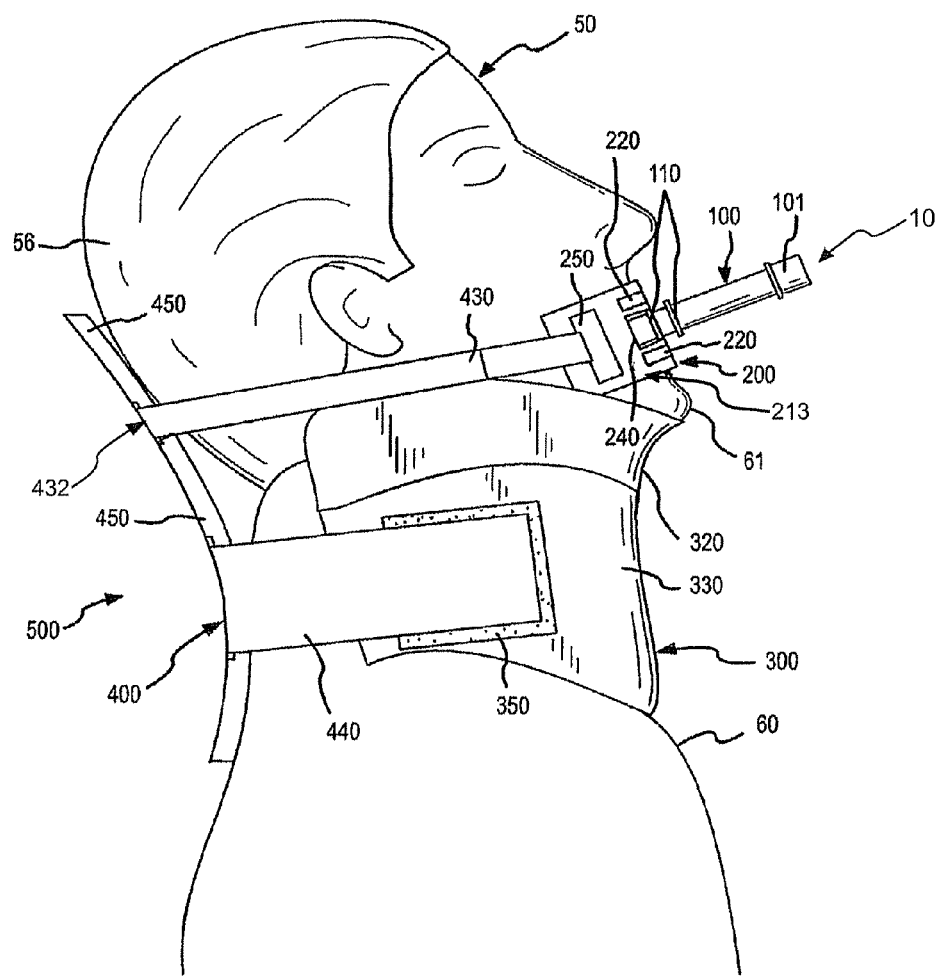
FIG. 1 is a side elevational view of an airway stabilization system which incorporates the present invention, shown applied to a patient.
Figure 2:
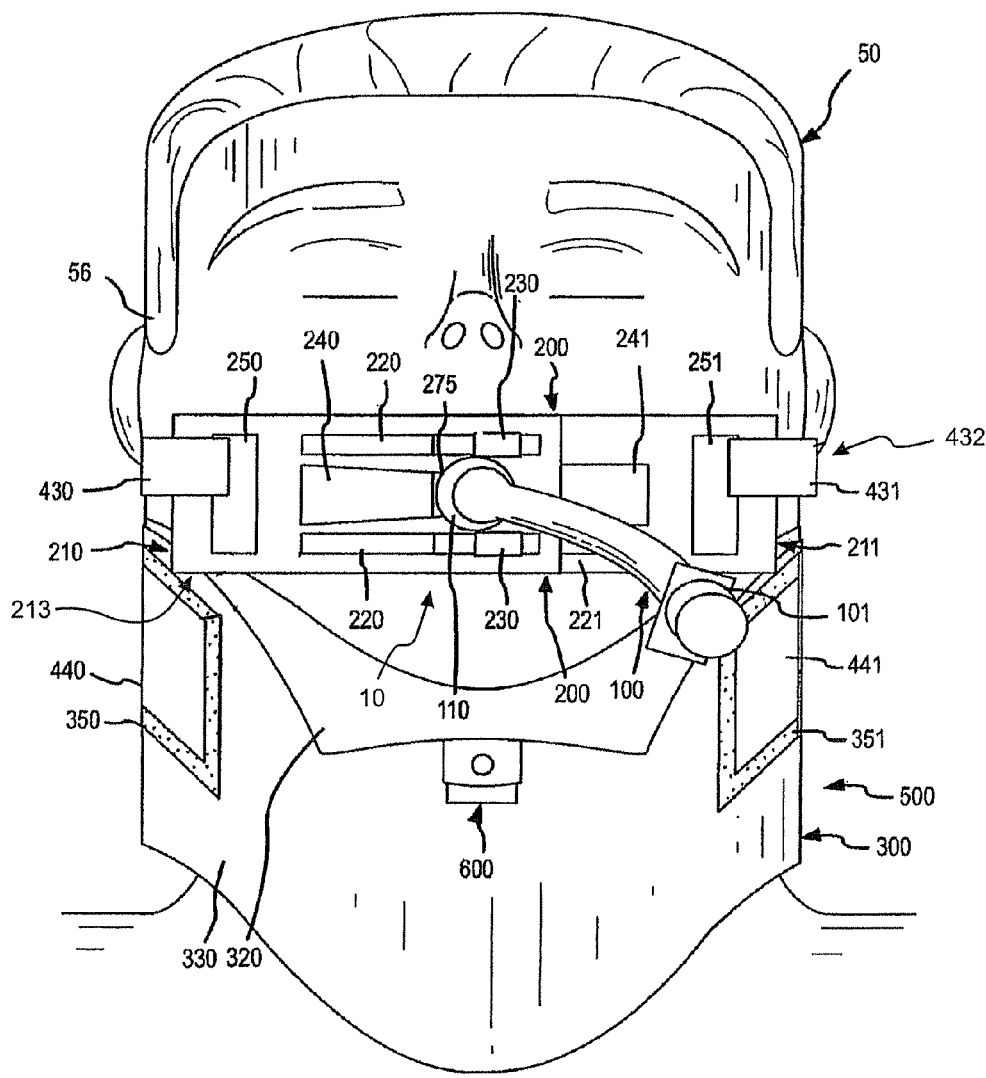
FIG. 2 is a front plan view of the airway stabilization system shown in FIG. 1.
Figure 3:
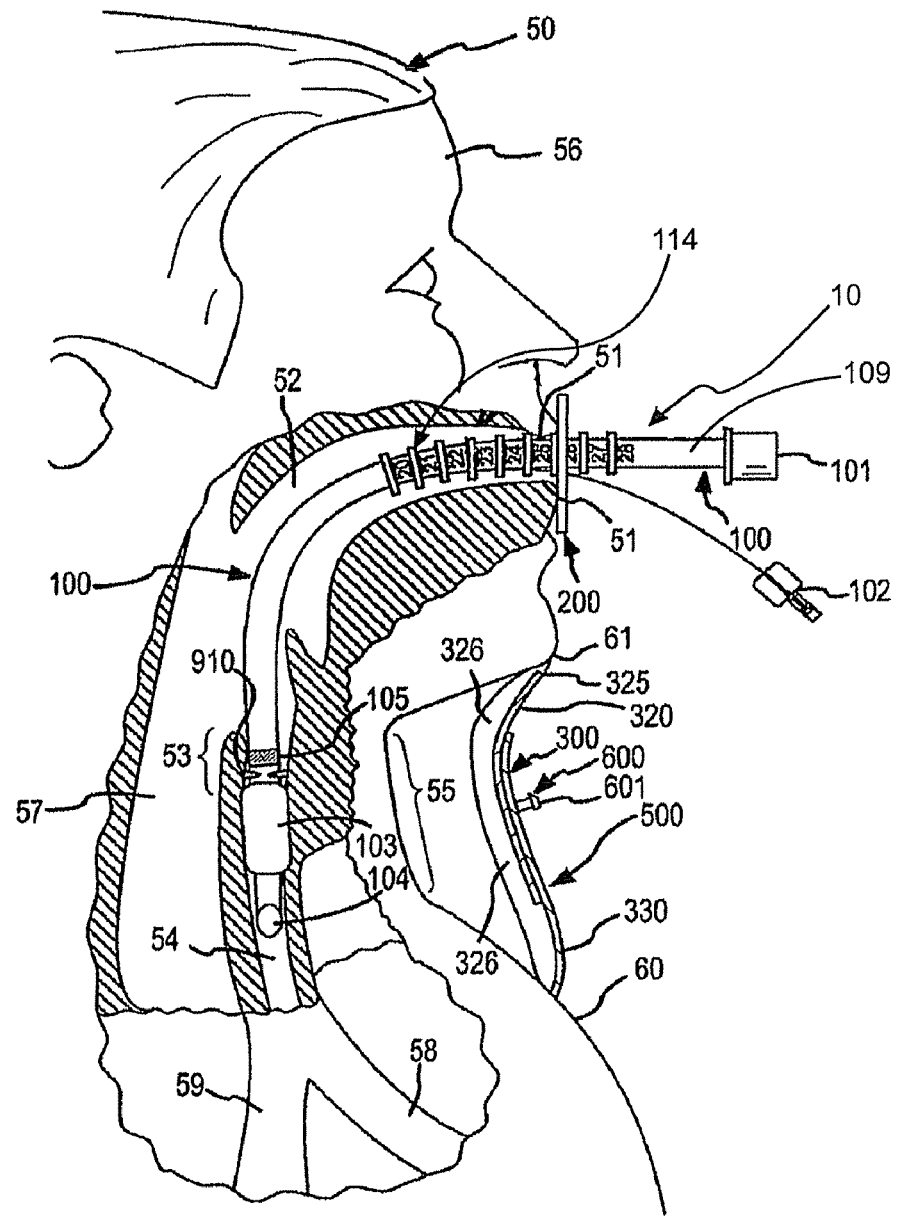
FIG. 3 is a side elevational view of the airway stabilization system shown in FIGS. 1 and 2, with certain portions broken away and shown in cross section, illustrating interaction with the anatomical structures of the patient.

A complete airway stabilization system 10 comprises which incorporates the present invention is shown in FIGS. 1, 2 and 3. The complete airway stabilization system is used to intubate a patient 50 under conditions where natural respiration is impossible or severely compromised. The airway stabilization system 10 establishes an air passageway to the lungs for respiration of the patient 50, while eliminating many of the risks and difficulties associated with intubation with an endotracheal tube.

The airway stabilization system 10 an endotracheal tube 100, a faceplate 200 and a stabilization collar 500. The endotracheal tube 100 is inserted through the mouth 51, throat 52 and larynx 53 of the patient 50 (FIG. 3), and into the trachea 54 by using conventional intubation procedures. The faceplate 200 fits over the patient's mouth 51 and interacts with the endotracheal tube 100 to restrain the endotracheal tube 100 relative to the faceplate 200. The stabilization collar 500 fits around the neck 55 of the patient 50. The faceplate 200 is affixed and retained relative to the stabilization collar 500. The stabilization collar 500 provides a structure for anchoring and restraining the faceplate 200 to hold the endotracheal tube 100 in a relatively stable position. The stabilization collar 500 also prevents or minimizes flexion and extension of the head 56 and neck 55, thereby preventing a distal end 104 of the endotracheal tube 100 from withdrawing from the larynx 53 and trachea 54 and moving into the esophagus 57 of the patient 50 and also preventing the distal end 104 of the endotracheal tube 100 from extending further through the trachea 54 and into one of the mainstem bronchial tubes 58 or 59 (FIG. 3). The relative retention of the endotracheal tube 100 and the faceplate 200, and the connection and retention of the faceplate 200 relative to the stabilization collar 500, and the immobilization of the head 56 and the neck 55 of the patient 50 by the stabilization collar 500, all combine to assure that the endotracheal tube 100 is established and maintained in the proper and correct position for intubation and respiration of the patient 50.

Figure 4:
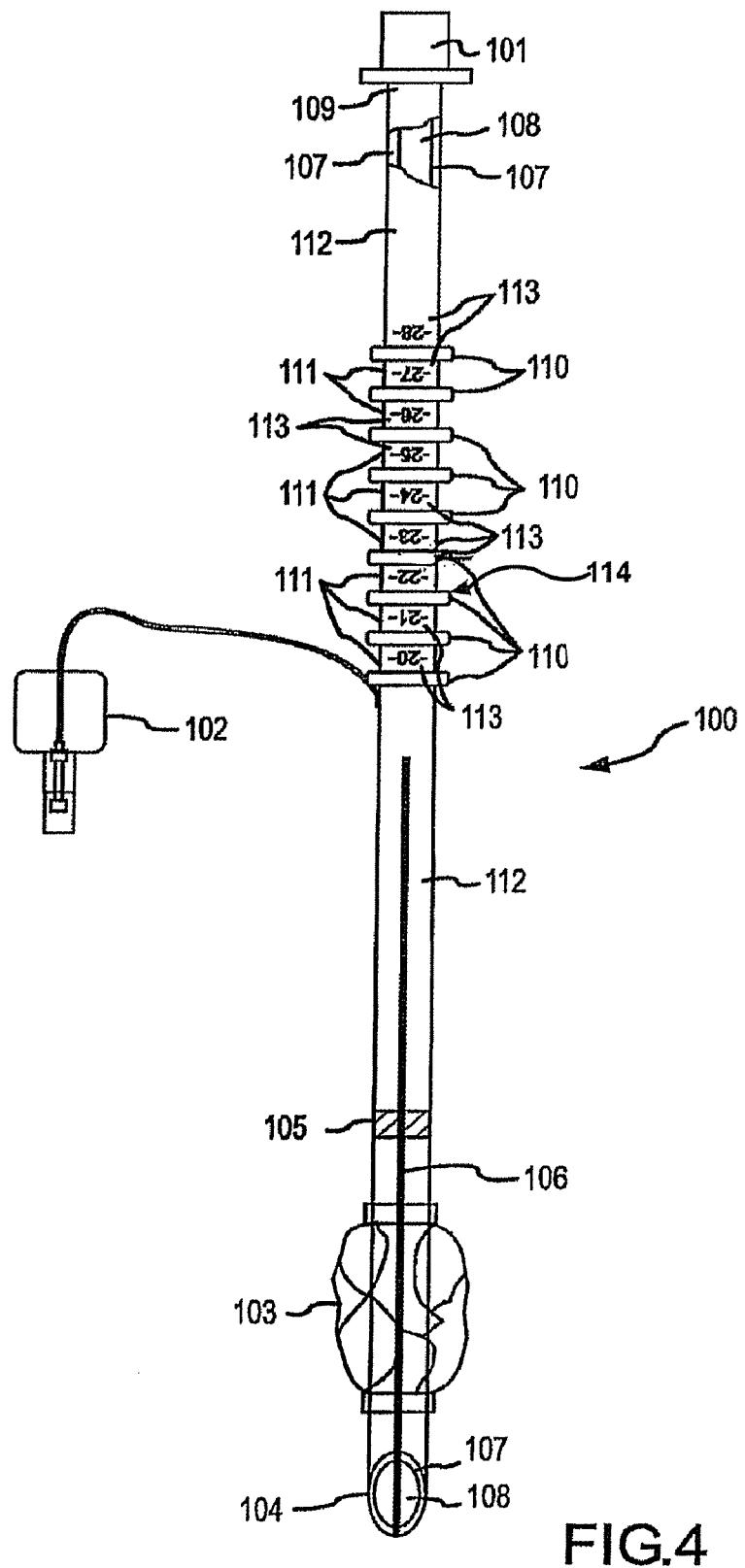
FIG. 4 is an elevational view of endotracheal tube, with a portion broken away, which forms one of the components of the airway stabilization system shown in FIGS. 1, 2 and 3.
Figure 5:
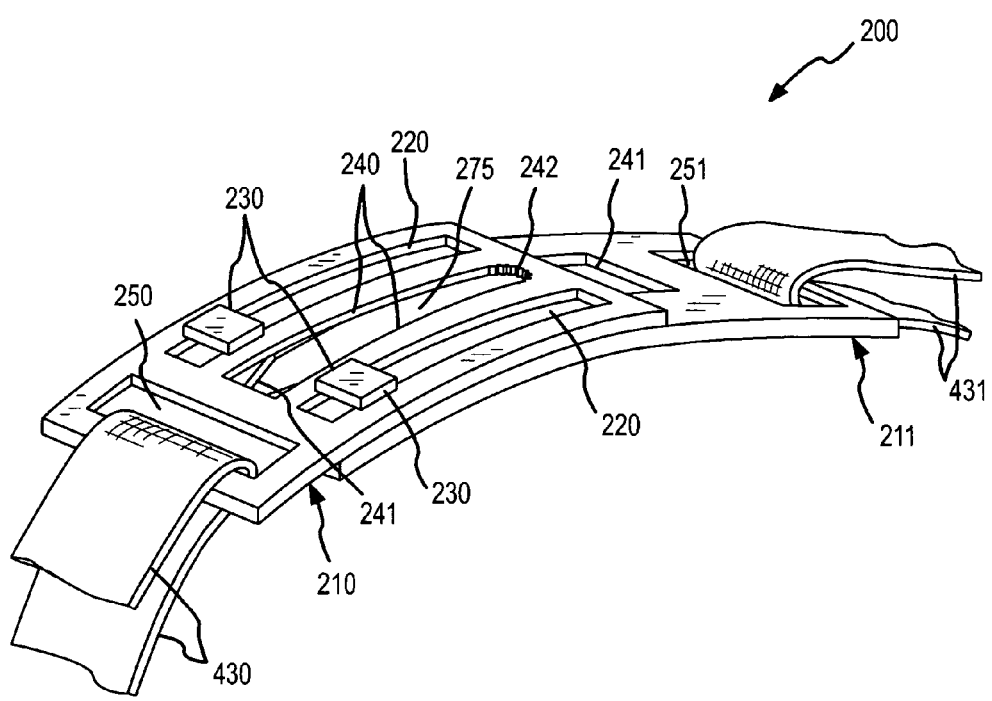
FIG. 5 is a perspective view of a faceplate which forms another one of the components of the airway stabilization system shown in FIGS. 1, 2 and 3, with portions of the fixation bands attached to the faceplate shown broken away.
Figure 6:
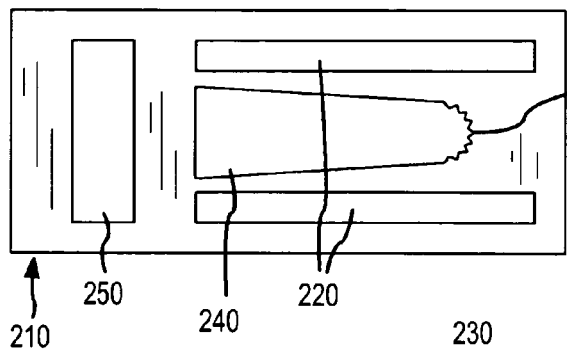
FIGS. 6 and 7 are plan views of upper and lower faceplate sections, respectively, of the faceplate shown in FIG. 5.
Figure 7:
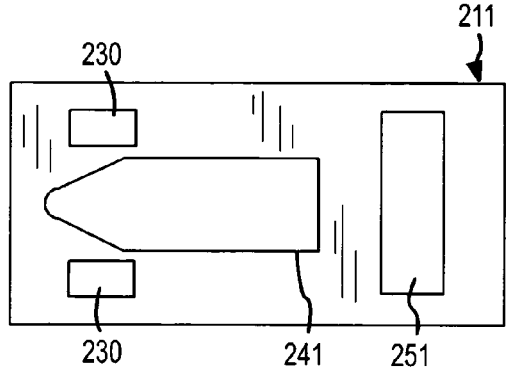
Figure 8:
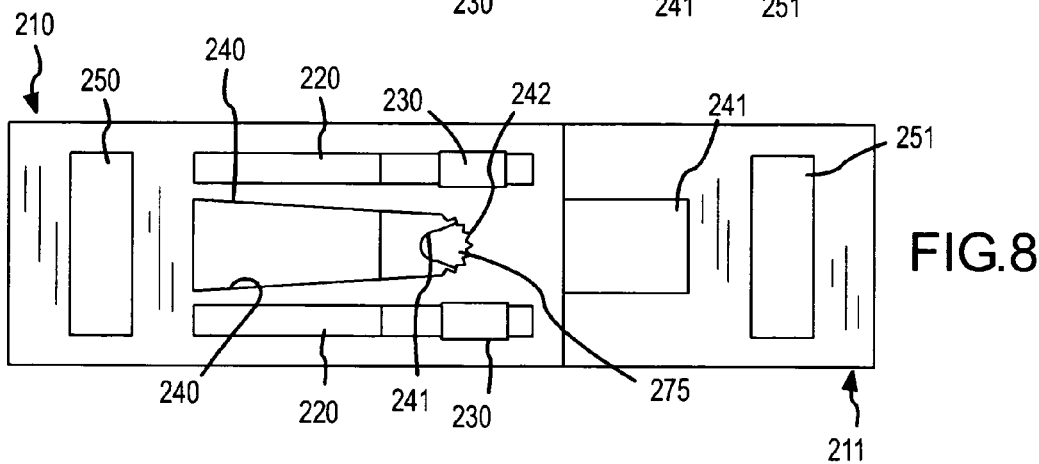
FIGS. 8 and 9 are plan views of the upper and lower faceplate sections shown in FIGS. 6 and 7, which have been assembled into the faceplate shown in FIG. 5, and which show relative movement of the faceplate sections away from one another and toward one another, respectively.
Figure 9:
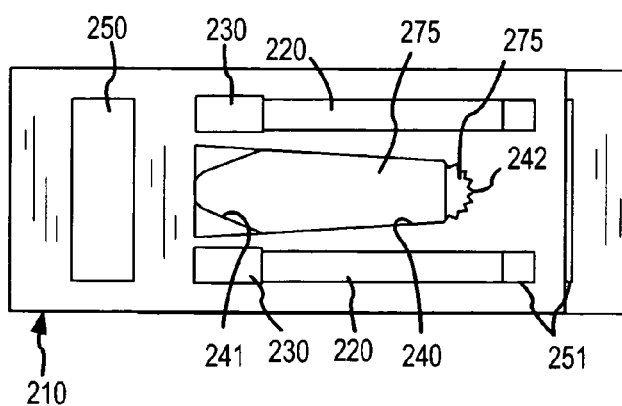
Figure 10:
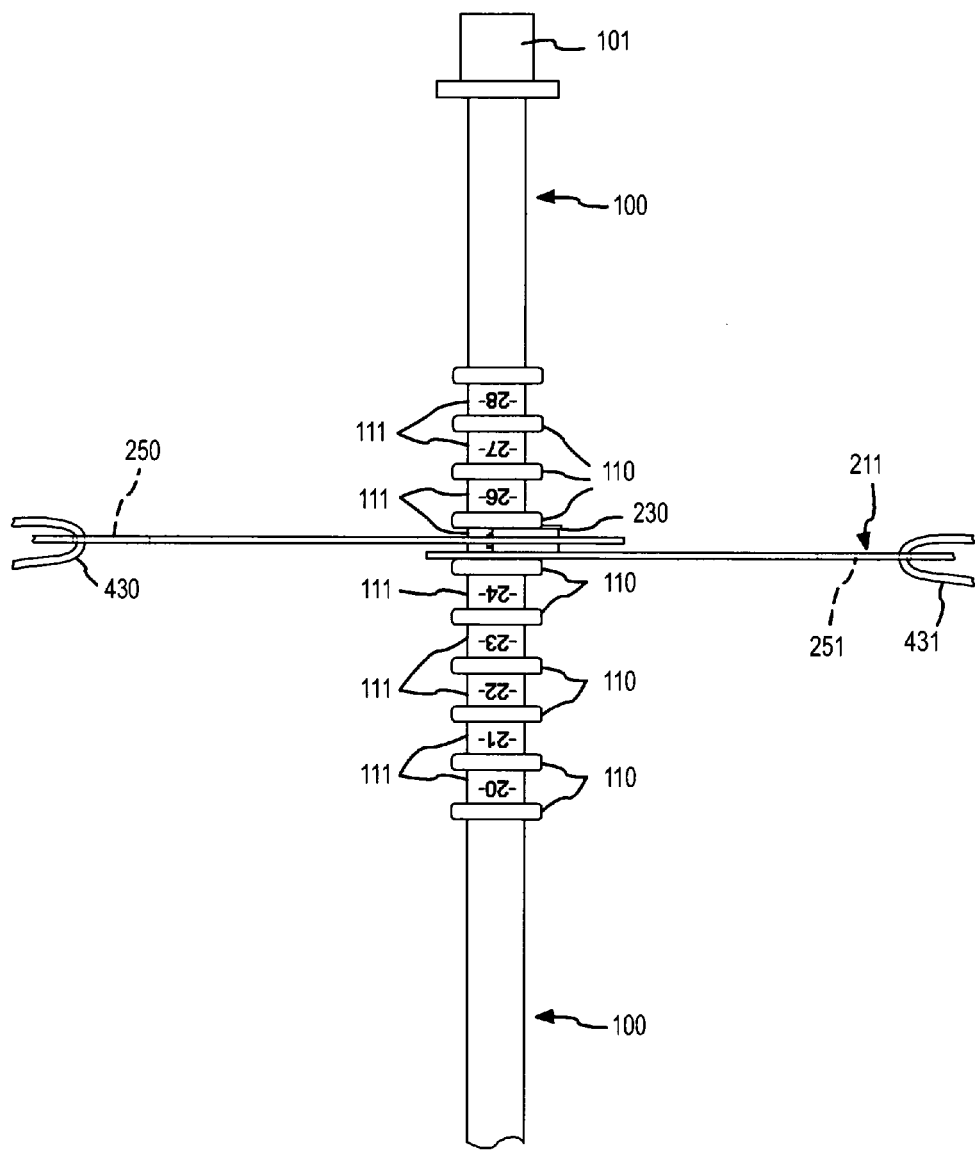
FIG. 10 is an elevational view showing the interaction of the endotracheal tube shown in FIG. 4 with the faceplate shown in FIG. 5, when used in the airway stabilization system shown in FIGS. 1, 2 and 3, with portions of the endotracheal tube and the faceplate shown broken away.

The endotracheal tube 100 includes a series of longitudinally-spaced protrusions or flanges 110, as shown in FIG. 4. Each of the flanges 110 has an exterior dimension greater than the exterior dimension of the main tubular body portion of the endotracheal tube 100, thereby creating a series of structural recesses 111 between adjacent pairs of the flanges 110 along a longitudinal segment of the tube 100. The flanges 110 and the structural recesses 111 are structured and arranged to form a retention structure 114. The faceplate 200 includes a pair of slidable overlapping faceplate sections 210 and 211, shown in FIG. 5. The inward and outward relative movement of the slidable overlapping faceplate sections 210 and 211 cooperatively create an expandable and contractible central orifice 275 in the faceplate 200. Expanding the central orifice 275, by moving the overlapping faceplate sections 210 and 211 toward one another as shown in FIG. 9, allows the endotracheal tube 100 to be inserted through the expanded central orifice 275, as shown in FIG. 2. The overlapping faceplate sections 210 and 211 are moved away from one another as shown in FIG. 8 to cause the central orifice 275 to contract around the endotracheal tube 100 at one of the recesses 111 of the retention structure 114, as shown in FIG. 10. The slidable overlapping faceplate sections 210 and 211 of faceplate 200 are structured and arranged to form a restraining device 213, which cooperates with retention structure 114 to restrain the position of the endotracheal tube 100, as also shown in FIG. 10. Fixation bands 430 and 431 extend from the overlapping sections 210 and 211, connect tautly to the stabilization collar 500, and are structured and arranged to form a fixation structure 432 which extends behind the patient's head to hold the restraining device in place, as shown in FIGS. 1 and 2. Tension in the fixation bands 430 and 431 holds the faceplate sections 210 and 211 in a position moved away from one another and causes the central orifice 275 to maintain its constricted contact with the tube 100 in the selected structural recess 111 (FIG. 10). In this manner, the overlapping faceplate portions 210 and 211 grip the endotracheal tube 100 at the central orifice 275, while the central orifice 275 is constricted sufficiently to be of a reduced cross-sectional size less than the cross-sectional size of the flanges 110, thereby creating a barrier beyond which the flanges 110 cannot pass and thus limiting movement of the endotracheal tube 100 relative to the faceplate 200.

The stabilization collar 500 includes an anterior portion 300 which is placed on the front of the patient's neck 55 and a posterior portion 400 which is placed on the back of the patient's neck 55. The anterior portion 300 of the stabilization collar 500 is adjusted vertically to fit along the length of the neck 55, thereby creating a restraint between the chest 60 and chin 61 (FIGS. 1 and 3) of the patient 50 to immobilize the patient's neck 55, thereby preventing the flexion and extension. Attachment straps 440 and 441, which are attached to the posterior portion 400 (FIG. 11), are pulled forward and attached to conventional hook and loop attachment pads 350 and 351 located on the anterior portion 300 of the stabilization collar 500 (FIGS. 1 and 2). When the attachment straps 440 and 441 are connected to the hook and loop attachment pads 350 and 351, the anterior portion 300 and the posterior portion 400 are firmly retained relative to one another while surrounding the neck 55.

Once the anterior and posterior portions 300 and 400 of the stabilization collar 500 have been connected, the fixation bands 430 and 431, which are also connected to the posterior portion 400, are extended through slots 250 and 251 of the overlapping faceplate sections 210 and 211, respectively. The free ends of the fixation bands 430 and 431 are attached back on the middle portion of the fixation bands 430 and 431, respectively, with conventional hook and loop attachments on the bands 430 and 431. The tension in the fixation bands 430 and 431 pull the overlapping faceplate sections 210 and 211 away from one another to constrict the central orifice 275 into one of the recesses 111 between the flanges 110 of the endotracheal tube 100 (FIG. 10) which has been selected to assure the proper depth position of the tube 100 within the trachea 54 (FIG. 3).

The connection of the anterior and posterior portions 300 and 400 of the stabilization collar 500 around the neck 55 of the patient 50 stabilizes and immobilizes the head 56 and neck 55 to assure that unanticipated flexion and extension movement of the head and neck will not displace the endotracheal tube 100 from its proper position within the trachea 54 (FIG. 3). The tension transferred through the fixation bands 430 and 431 between the stabilization collar 500 and the overlapping faceplate sections 210 and 211 assures that the central orifice 275 firmly grips and retains the endotracheal tube 100 between a pair of flanges 110 (FIG. 10). The tension from the fixation bands 430 and 431 also assures that the faceplate 100 will be in the desired position on the face of the patient 50. In this manner, complete stabilization of the endotracheal tube 100 is achieved to assure an open air respiration passageway into the lungs.

More details concerning the endotracheal tube 100 are shown in FIGS. 4 and 10. The endotracheal tube 100 includes a conventional ventilation conduit connector fitting 101 and a conventional inflation connector fitting 102. The conduit connector fitting 101 is located at a proximal end 109 of the tube 100, and the inflation connector fitting 102 is located near the proximal end 109 of the tube 100 (FIG. 3). The conduit connector fitting 101 is used to connect an air conduit (not shown) from a conventional ventilation device (also not shown) to the endotracheal tube 100. The ventilation device supplies respiratory air to the lungs through the endotracheal tube 100. The respiratory air flows through a hollow interior conduit 108 that extends from the distal end 104 of the endotracheal tube 100 to the proximal end 109. The continuous main tubular body 107 of the endotracheal tube 100 confines the respiratory airflow to the hollow interior conduit 108. The inflation connector fitting 102 is used to conduct air into a conventional expandable cuff or balloon 103 located at the distal end 104 of the tube 100. Once the endotracheal tube 100 has been properly positioned with the distal end 104 within the trachea 54, air inserted through the inflation connector fitting 102 inflates the balloon 103 against the sidewall of the trachea 54 (FIG. 3). Inflating the balloon 103 against the sidewall of the trachea 54 assures that all of the respiratory air flowing into and out of lungs passes through the endotracheal tube 100. In this manner, the lungs of the patient 50 may be expanded by air pressure and then allowed to contract in a manner which establishes artificial respiration, if necessary. Inflating the balloon 103 against the sidewall of the trachea 54 also protects the airway into the lungs by preventing fluid from draining into the lungs. In the present description, the terms "proximal" and "distal" are in relation to the medical practitioner who inserts the endotracheal tube 100, and not in relation to the patient who receives the endotracheal tube 100.

The endotracheal tube 100 includes the multiple ring-like protrusions or flanges 110 which extend outward from the exterior surface 112 of the tube 100. Preferably, each of the flanges 110 is integrally formed as a part of the main tubular body 107 of the endotracheal tube 100, although separate ring-like flanges 110 could also be permanently attached on the exterior surface 112 of the main tubular body 107 with an adhesive, for example. Each of the adjoining flanges 110 is separated by a distance of approximately 1 cm. When the faceplate sections 210 and 211 are moved away from one another to constrict the central orifice 275 around the endotracheal tube 100, the distance across the central orifice 275 (FIG. 5) is smaller than the maximum diameter or distance across the flanges 110, thus creating a barrier to longitudinal movement of the tube 100 when a flange 110 contacts the faceplate sections 210 and 211 at the central orifice 275.

The flanges 110 are also spaced at predetermined distances from the distal end 104 of the endotracheal tube 100. Spacing the flanges 110 in this manner allows one recess 111 to be selected to establish the proper depth for insertion of the endotracheal tube 100 into the trachea 54 in relation to the patient's mouth 51 (FIG. 3). The recess 111 between the flanges 110 which is identified in this manner is the selected recess around which the central orifice 275 in the faceplate sections 210 and 211 is placed and constricted. The series of flanges 110 preferably begin at 19.5 cm from the distal end 104 of the tube 100 and are spaced apart at the 1 cm intervals until reaching the distance at 28.5 cm from the distal end 104. A series of the flanges 110 along this segment of the endotracheal tube 100 will accommodate the different sizes in an anatomy of the vast majority of patients. The recesses 111 between adjacent pairs of flanges 110 therefore become depth localizer regions, each of which is preferably marked (FIGS. 4 and 10) with a number or other indication 113 that signifies the length in centimeters from the center of that recess 111 to the tip at the distal end 104 of the tube 100. For example, the center point of the recess 111 which is marked with the numeral "20" is located 20 cm from the tip at the distal end 104 of the endotracheal tube 100, and the center point of recess 111 which is marked with the numeral "28" is located 28 cm from the tip at the distal end 104 of the endotracheal tube 100.

The endotracheal tube 100 also includes a vocal cord indicator or locator band 105, shown in FIG. 4. The vocal cord locator band 105 is formed by a dark color peripheral mark or indication around the circumference of the tube 100 at a location approximately 2 cm proximal to the inflatable balloon 103. The endotracheal tube 100 is inserted until the locator band 105 is observed to be just proximal to the level of the vocal cords 910 within the larynx 53 (FIG. 3), at which point the most proximal portion of the inflatable balloon 103 will be located approximately 2 cm distal to the vocal cords 910. In this position, the endotracheal tube 100 is located at the proper insertion depth within the trachea 54 for intubation.

In addition, a radio-opaque stripe 106 may be formed along the length of the distal portion of the endotracheal tube 100. The radio-opaque stripe 106 is identifiable in a conventional chest x-ray to allow comparison of location of the stripe 106, and hence the distal end of the endotracheal tube 100, to known anatomical structures. In this manner, the positioning of the endotracheal tube 100 can be facilitated and confirmed radiographically.

More details concerning the faceplate 200 are shown in FIGS. 1-3 and 5-10. Each of the faceplate sections 210 and 211 has a general rectangular configuration. Each faceplate section 210 and 211 is formed of thin plastic or other material which is essentially rigid in a longitudinal dimension but which is sufficiently flexible in an orthogonal dimension. The flexibility in the orthogonal dimension allows the faceplate sections 210 and 211 to generally bend around and conform to that portion of the face of the patient 50 surrounding the mouth of 51 (FIG. 3).

The two faceplate sections 210 and 211 are overlapped and connected together to permit relative movement of the two sections 210 and 211 toward and away from each other. The sliding movement is permitted by a pair of male protrusions 230 on the lower faceplate section 211 extending into a pair of correspondingly-located female channels 220 in the upper faceplate section 210. Relative sliding movement of the faceplate sections 210 and 211 toward and away from one another is permitted as a result of the male protrusions 230 moving along the female channels 220.

The faceplate sections 210 and 211 each include overlapping lateral openings 240 and 241, respectively. The lateral opening 240 in the faceplate section 210 extends essentially parallel to the female channels 220. The lateral opening 241 in the faceplate section 211 is located between the male protrusions 230 and is aligned with and overlaps the lateral opening 240 in the faceplate section 210 when the sections 210 and 211 are connected together and move toward and away from one another. The right hand portion of the lateral opening 240 (as shown) and the left-hand portion of the lateral opening 241 (as shown) overlap with one another to establish and define the central orifice 275 through the faceplate 200. The endotracheal tube 100 extends through the central orifice 275 (FIGS. 1-3, 10). Because the right hand portion (as shown) of the lateral opening 240 and the left hand portion (as shown) of the lateral opening 241 each converge inwardly to reduce the transverse width of the opening 240 and 241, the dimension of the central orifice 275 is diminished by moving the faceplate sections 210 and 211 in a relative direction away from one another.

The extreme right hand portion (as shown in FIGS. 5, 6, 8 and 9) of the lateral opening 240 is generally semicircular in configuration, and a series of serrations 242 is formed to face into the lateral opening 240 along the semicircular portion of that opening 240. The serrations 242 create teeth which are useful for increasing the amount of gripping restraint supplied to the endotracheal tube 100 in the recess 111 between the flanges 110.

When the two faceplate sections 210 and 211 are moved toward one another, as shown in FIG. 9, the overlap of the lateral openings 240 and 241 increases in the size and the central orifice 275 expands or opens to its maximum size. With the central orifice 275 at or near its maximally open position, the faceplate 200 may be placed over the endotracheal tube 100 by extending the proximal end 109 of the tube 100, the ventilation conduit connector fitting 101 and the inflation connector fittin 102 through the central orifice 275. The central orifice 275 is moved along the flanges 110 of the endotracheal tube 100 until the two overlapped faceplate sections 210 and 211 are positioned over a selected depth localizer recess 111, such as the recess marked "25" shown in FIG. 10. The selected recess marked "25" is located 25 cm from the distal end 104 of the endotracheal tube 100.

The two sections 210 and 211 of the faceplate 200 are moved or pulled apart relative to one another, as shown in FIG. 8, and the two overlapped lateral openings 240 and 241 of the faceplate sections 210 and 211 constrict the size of the central orifice 275. The size of the central orifice 275 is reduced until the overlapping lateral openings 240 and 241 in the faceplate sections 210 and 211 have tightly constricted around the endotracheal tube 100 within the selected recess 111 (e.g., that recess marked "25" shown in FIG. 10), thus firmly gripping the tube 100 and restraining the tube 100 against longitudinal movement beyond the flanges 110 which define the selected recess 111. The fixation bands 430 and 431 which extend through the slots 250 and 251 in the sections 210 and 211, respectively, are then drawn taut by introducing a slight amount of tension in the fixation bands 430 and 431 due to by their attachment to the stabilization collar 500. The slight amount of tension in the fixation bands 430 and 431 biases the faceplate sections 210 and 211 of the faceplate 200 apart from one another, thereby assuring that the central orifice 275 is constricted firmly around the endotracheal tube 100 at the selected recess 111. The tension in the fixation bands 430 and 431 maintains the constriction of the central orifice 275 within the selected recess 111 and prevents the central orifice 275 from expanding sufficiently to allow the endotracheal tube to move further beyond the two flanges 110 which define the selected recess 111. In this manner, the endotracheal tube 100 and the faceplate 200 are affirmatively mechanically retained or fixed relative to one another. The bands 430 and 431 and the slots 250 and 251 through which the fixation bands 430 and 431 respectively extend, are one example of a fixation structure for retaining the faceplate sections 210 and 211 relative to one another and constricted around the selected recess of the endotracheal tube. Another example of a fixation structure would be mechanical connection (not shown) which operates directly between the faceplate sections 210 and 211, while separate bands similar to the fixation bands 430 and 431 retain the faceplate in position at the mouth of the patient.

FIG. 10 illustrates that if the endotracheal tube 100 is pulled or pushed sufficiently to overcome the gripping action of the lateral openings 240 and 241 against the endotracheal tube 100 at the constricted central orifice 275, the contact of the faceplate 200 with the flanges 110 creates a barrier which prevents and limits further movement. Inward or outward movement of the tube 100 is limited to the 1 cm distance between adjacent flanges 110. The contact of a flange 110, whose outside diameter or transverse distance is greater than the constricted size across the central orifice 275, with the faceplate 200 prevents further movement of the endotracheal tube 100.

Figure 11:
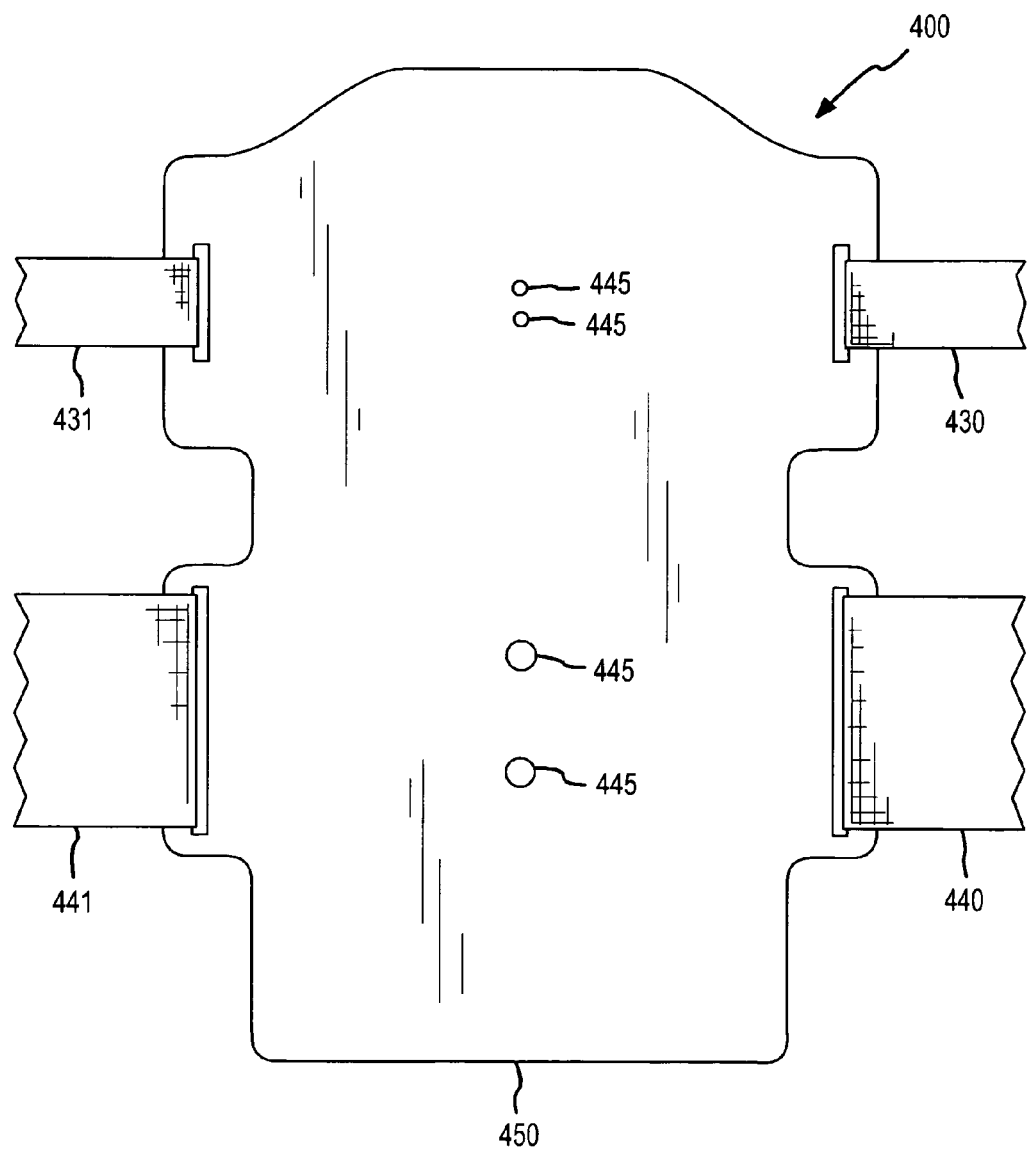
FIG. 11 is an inside elevational view of a posterior portion of a stabilization collar of the airway stabilization system shown in FIGS. 1, 2 and 3, with portions of fixation bands and attachment straps shown broken away.
Figure 12:
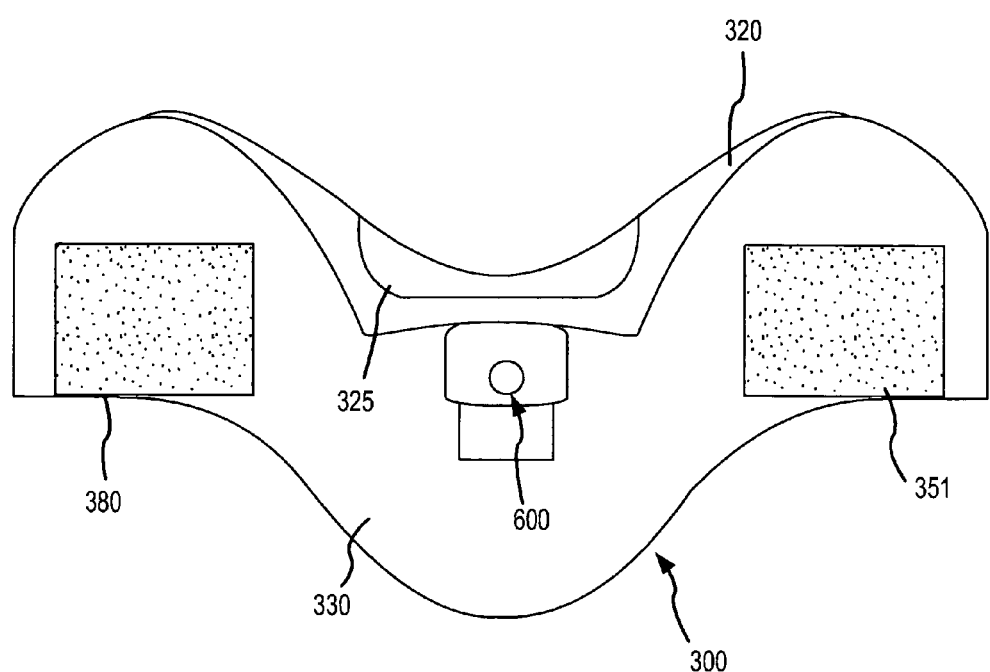
FIG. 12 is an outside elevational view of an anterior portion of a stabilization collar of the airway stabilization system shown in FIGS. 1, 2 and 3.

More details concerning the stabilization collar 500 are shown in FIGS. 1-3 and 11-23. As shown in FIG. 1, the posterior portion 400 of the stabilization collar 500 comprises an elongated main posterior support 450 which is sufficiently long to extend between the back of the head 56 and the spinal column of the patient 50 immediately adjacent to the neck. The fixation bands 430 and 431 and the attachment straps 440 and 441 are also connected to the posterior support 450 with fasteners such as rivets 446 and 445, as shown in FIG. 11. The lower attachment straps 440 and 441 connect to the attachment pads 350 and 351 located on the anterior portion 300 of the stabilization collar 500, as shown in FIGS. 1 and 2. Tautly connecting the lower attachment straps 440 and 441 to the anterior portion 300 causes the anterior and posterior portions of 300 and 400 to attach or connect together and to encircle the neck 56 of the patient 50 as a unit, thereby immobilizing or substantially limiting any flexion or extension of the head and neck. The upper fixation bands 430 and 431 hold the faceplate 200 to the patient's face as well as hold the overlapping faceplate sections 210 and 211 in position moved apart from one another to constrict the central orifice 275 around the selected recess 111 between the flanges 110 of the endotracheal tube.

The anterior portion 300 of the stabilization collar 500 comprises two overlapping components 320 and 330, as shown in FIGS. 3 and 12-14. The lower component 330 contacts the chest 60 of the patient, and the upper component 320 includes a chin support 325 which contacts the chin 61 of the patient. Flexible padding 326 is located on the inside of the components 320 and 332 cushion the contact of the anterior portion 300 with the chin 61, chest 60 and other portions of the neck 56 of the patient. The lower component 330 is spaced outward from the upper component 320. The hook and loop attachment pads 350 and 351 (FIGS. 1, 2 and 12) for the attachment straps 440 and 441 are formed on the lower and forward component 320.

Figure 13:
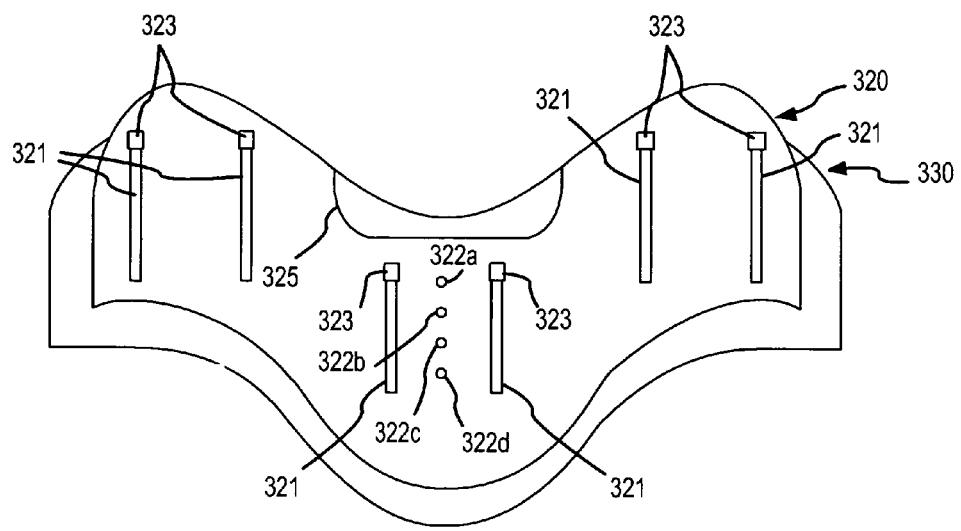
FIGS. 13 and 14 are inside elevational views of the anterior portion of the stabilization collar shown in FIG. 12, with portions broken away, to reveal the relative positioning of two components of the anterior portion during vertical height adjustment.
Figure 14:
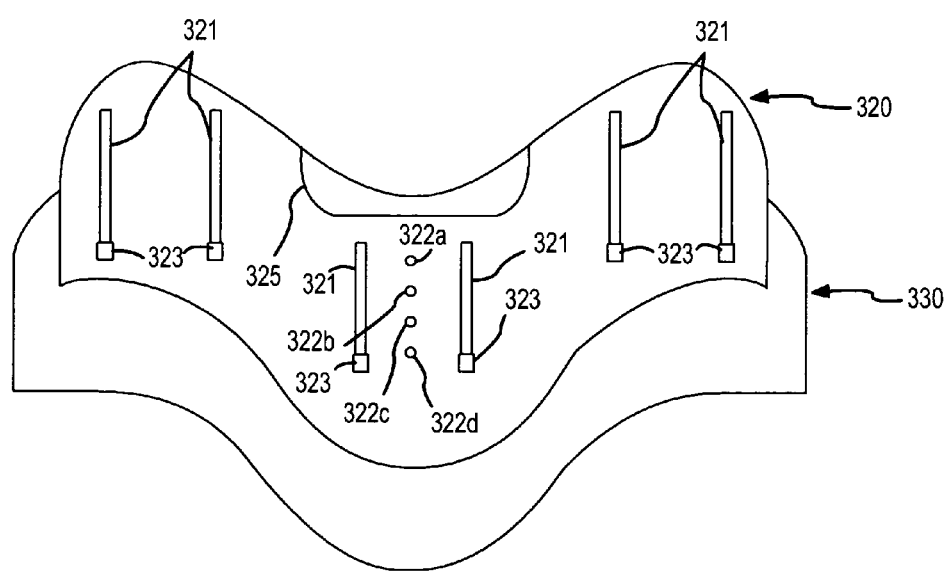
Figure 15:
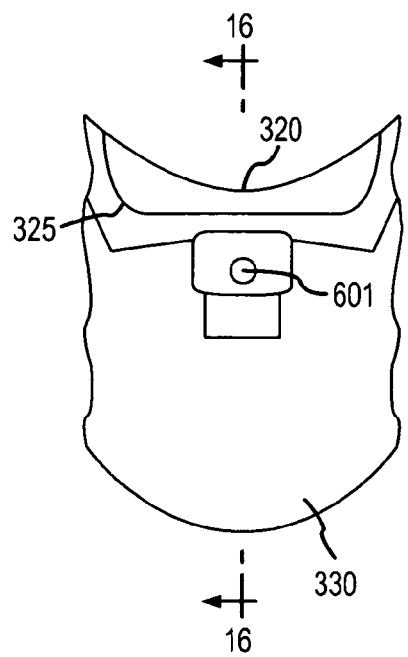
FIG. 15 is a partial outside view of the anterior portion of the stabilization collar shown in FIG. 12, adjusted to extend to a relatively lesser vertical height.
Figure 16:
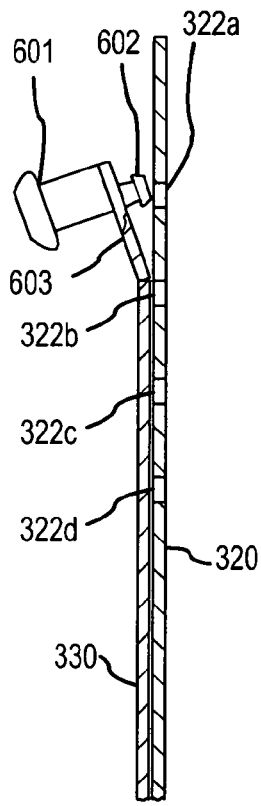
FIG. 16 is a cross-sectional view of a the anterior portion of the stabilization collar shown in FIG. 15, taken substantially in the plane of line 16-16 in FIG. 15.

The two components 320 and 330 are adjustable vertically with respect to one another to accommodate differences in length between the chest 60 and the chin 61 of the patient 50 (FIG. 3), as is shown in FIGS. 13-19. FIGS. 13 and 14 are views of the components 320 and 330 looking outward or forward from the interior of the anterior portion 300 with padding 326 (FIG. 3) not shown to illustrate some of the adjustment mechanisms of the components 320 and 330.

The lower and forward component 330 has three pairs of male protrusions 323 that project rearwardly into three pairs of vertically-extending female channels 321 in the upper and rear component 320, as understood from FIGS. 13 and 14. The extension of the three pairs of male protrusions 323 into the three pairs of female channels 321 allow the two components 320 and 330 to slide vertically in relation to each other. The vertical movement allows longitudinal adjustment to accommodate the different lengths between the chest 60 and chin 61 of many different patients 50. After the components 320 and 330 of the anterior portion 300 are appropriately adjusted, the adjusted position is locked into place with a locking mechanism 600.

Figure 17:
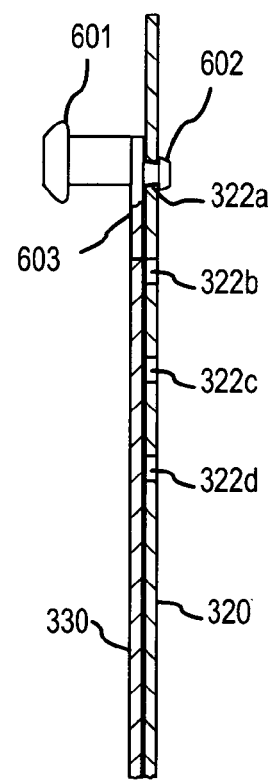
FIG. 17 is a cross-sectional view similar to FIG. 16, showing another position of a locking mechanism of the anterior portion of the stabilization collar.
Figure 18:
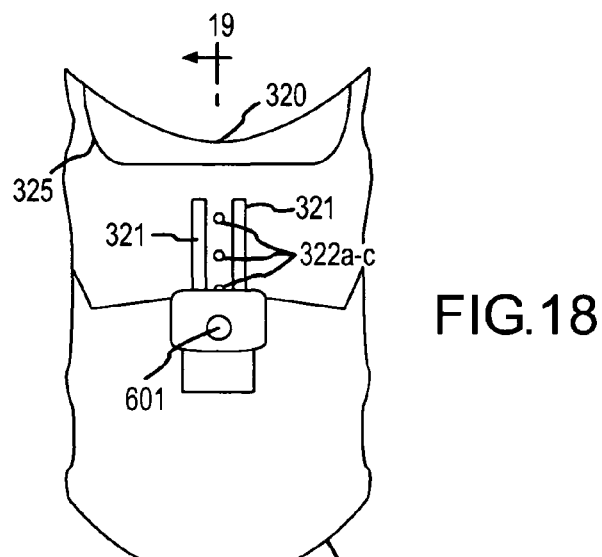
FIG. 18 is a partial outside view of the anterior portion of the stabilization collar shown in FIG. 12, adjusted to extend to a relatively greater vertical height.
Figures 19, 20:
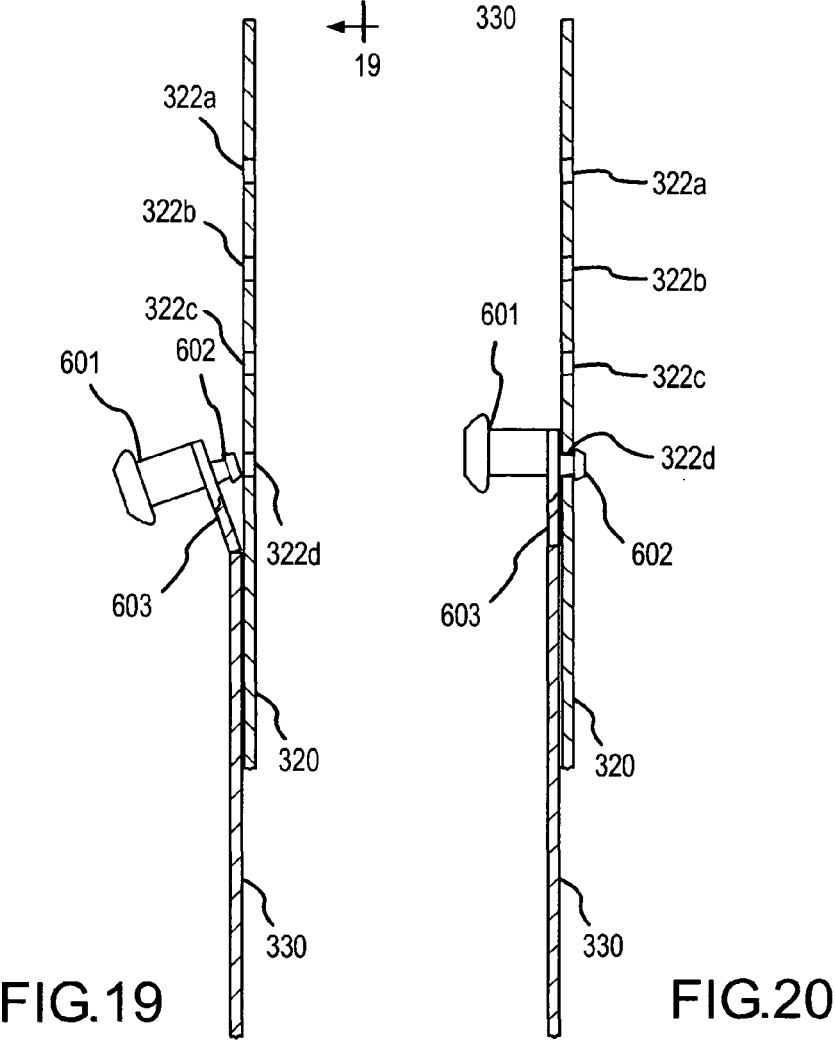
FIG. 19 is a cross-sectional view of the anterior portion of the stabilization collar shown in FIG. 18, taken substantially in the plane of line 19-19 in FIG. 18.
FIG. 20 is a cross-sectional view similar to FIG. 19, showing another position of a locking mechanism of the anterior portion of the stabilization collar.

The locking mechanism 600 is shown in detail in FIGS. 15-20. The locking mechanism 600 comprises a push-pull plunger 601 which includes a detent 602 that is selectively extended through one of a series of longitudinally spaced receiving holes 322a, 322b, 322c or 322d formed in the upper and rear component 320. The plunger 601 is connected to a living hinge flap 603 of the lower and forward component 330. The receiving holes 322a, 322b, 322c and 322d are aligned between the female channels 321 in a vertical line below the detent 602 of the plunger 601. When components 320 and 330 are moved vertically in relation to each other to achieve the proper chin 61 to chest 60 (FIG. 3) length, the plunger 601 is grasped and pushed to extend the detent 602 into the one of the receiving holes 322a, 322b, 322c or 322d that is aligned with the detent 602 to achieve the proper chin-to-chest length. FIG. 17 illustrates engaging the detent 602 with the receiving hole 322a to achieve the smallest chin-to-chest length, while FIG. 20 illustrates engaging the detent 602 with the receiving hole 322d to achieve the greatest chin-to-chest length. Engaging the detent 602 with the receiving holes 322b and 322c adjusts the components 320 and 330 for medium chin-to-chest lengths. If subsequent adjustment of the two components 320 and 330 is required after initially establishing the relative height of the components 320 and 330, the plunger 601 is grasped and pulled to remove the detent 602 from one of the receiving holes 322a, 322b, 322c or 322d. With the detent 602 removed from the receiving holes, the components 320 and 330 are thereafter moved relative to one another until a different receiving hole is located below the detent 602. The detent 602 is extended through that receiving hole to hold for components 320 and 330 in the newly adjusted position. The padding 326 (FIG. 3) is sufficiently flexible to permit vertical adjustment of the components 320 and 330.

Figure 21:
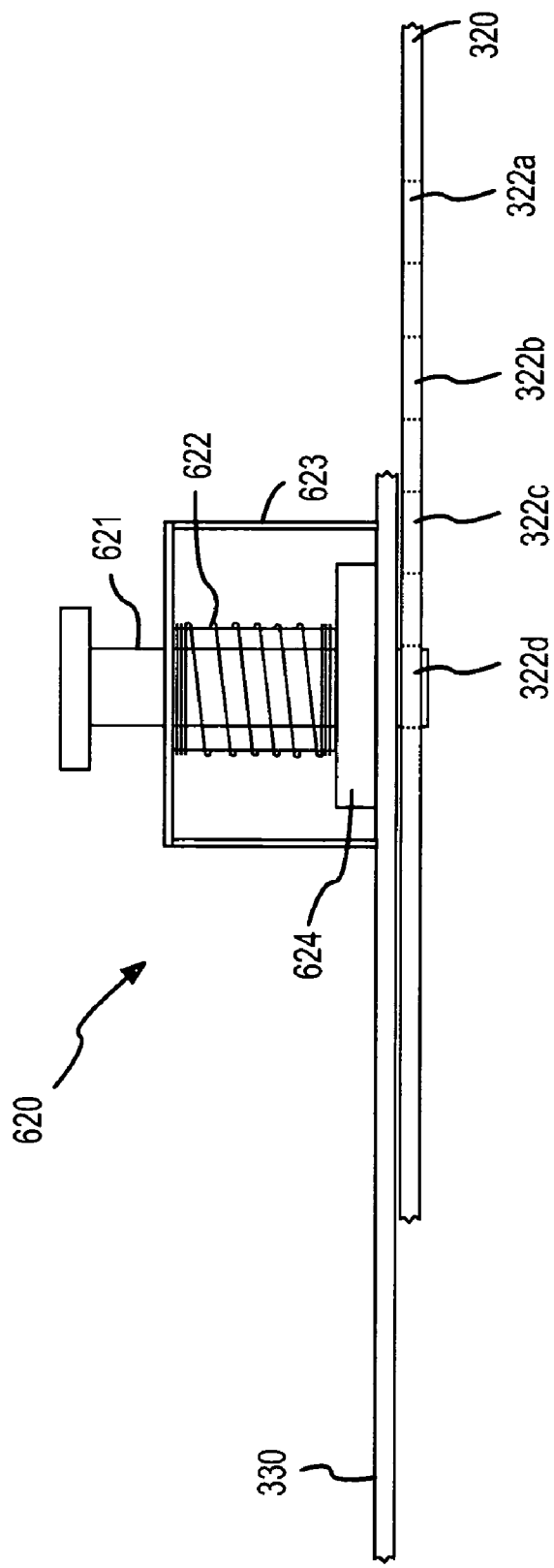
FIG. 21 is a vertical section view of a locking mechanism which is an alternative to the locking mechanism shown in FIGS. 15-20.

Another type of locking mechanism, which is an alternative to the locking mechanism 600, is a conventional pull-latch locking mechanism 620, shown in FIG. 21. The pull-latch locking mechanism 620 includes a plunger 621 which is extended through one of the receiving holes 322a, 322b, 322c or 322d (FIGS. 17-18, 19-20) to retain the components 320 and 330 of the anterior portion 300 relative to one another. The pull-latch locking mechanism 620 includes a housing 623 which contains the plunger 621 and a spring 622. The spring 622 extends between the inside of the housing 623 and a flange 624 formed on the plunger 621 within the interior of the housing 623. The spring 622 normally biases the lower end of the plunger 621 downward, into one of the receiving holes 322a, 322b, 322c or 322d. The portion of the plunger 621 which extends outside of the housing 623 is gripped to pull the plunger 621 outward relative to the housing 623 against the normal bias forced from the spring 622. The upward movement of the plunger 621 disengages its lower end from one of the receiving holes 322a, 322b, 322c or 322, thereby allowing relative movement of the components 320 and 330 to adjust the vertical height of the anterior portion 300 of the stabilization collar.

Figure 22:
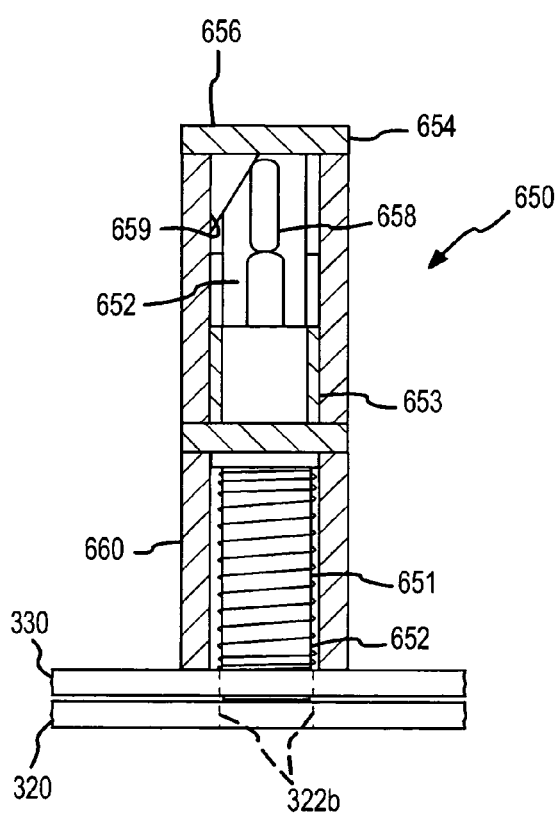
FIGS. 22 and 23 are vertical section views of a locking mechanism which is another alternative to the locking mechanisms shown in FIGS. 15-20 and 21.
Figure 23:
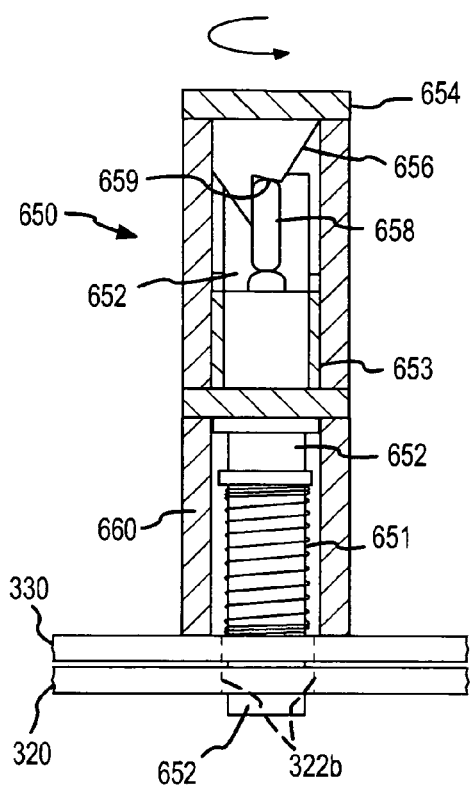

Another type of locking mechanism, which is an alternative to the locking mechanisms 600 and 620, is a conventional rotary-cam locking mechanism 650, shown in FIGS. 22 and 23. The rotary-cam locking mechanism 650 includes a plunger 652, the lower end of which is extended through one of the receiving holes 322a, 322b, 322c or 322d (FIGS. 17-18, 19-20) to retain the components 320 and 330 of the anterior portion 300 relative to one another. The rotary-cam locking mechanism 650 includes a housing 660 which contains the plunger 652 and a spring 651. The spring 651 normally biases the lower end of the plunger 652 upward, out of the receiving holes 322a, 322b, 322c or 322d. A cap 654 is rotationally attached to the top of the housing 660. An upper portion of the plunger 652 extends into an interior hollow portion of the cap 654. The plunger 652 is prevented by rotating by projections (not shown) on the plunger 652 which extend within slots (not shown) of a slotted stationary sleeve 653 that is attached stationarily relative to the housing 660. The upper end of the plunger 652 includes a pair of projections 658 which extend from opposite sides of the plunger 652. The projections 658 contact and interface with angled cam surfaces 656 on the inside of the cap 654.

When the cap 654 is rotated (counterclockwise as shown), the cam surfaces 656 push downward on the projections 658, moving the plunger 652 downward against the bias force from the spring 651 until the projections 658 reach the lowermost edge of the cam surface 656 (as shown). Slight further rotational movement of the cap 654 moves each of the projections 658 into a reverse angled retaining notch 659. Retaining notches 659 are formed on opposite sides of the interior of the cap 654. Because the retaining notch 659 is angled in the opposite direction of the cam surface 656, the projections 658 rest in the retaining notch 659 and are held in this position by the bias from the spring 651. In this position, the lower end of the plunger 652 extends through one of the receiving holes 322a, 322b, 322c or 322d, thereby retaining the two components 320 and 330 of the anterior portion 300 in a fixed position relative to one another.

Rotation of the cap 654 in the opposite direction releases the projections 658 from the retaining notch 659, and allows the plunger 652 to move upward in response to the bias force from the spring 651. The upward movement of the plunger 652 disengages its lower end from one of the receiving holes 322a, 322b, 322c or 322, thereby allowing relative movement of the components 320 and 330 to adjust the vertical height of the anterior portion 300 of the stabilization collar.

The airway stabilization system described above is used as follows. The endotracheal tube 100 is passed through the mouth 51, throat 52 and larynx 53 and into the trachea 54. The endotracheal tube 100 is passed between the vocal cords 910. The tube 100 is advanced until the vocal cord locator band 105 is immediately proximal to the level of the vocal cords 910. The balloon 103 is then inflated.

While holding the correctly placed endotracheal tube 100 to prevent its movement, the posterior portion 400 of the stabilization collar 500 is placed behind the patient's neck 55. The anterior portion 300 of the stabilization collar 500 is adjusted vertically to establish the correct chest-to-chin length for the patient, and the anterior portion 300 and placed over the front of the patient's neck 55. The attachment straps 440 and 441 are pulled forward from the posterior portion 400 and attached to the hook and loop attachment pads 350 and 351 on the anterior portion 300 of the stabilization collar 500, thereby securing the anterior and posterior portions 300 and 400 together to immobilize the neck 55 and head 56.

With the stabilization collar 500 and the endotracheal tube 100 both in place, the depth localizer region provided by a recess 111 between the flanges 110 at the level of the mouth 51 is identified. The two overlapping faceplate sections 230 and 231 of the faceplate 200 are slid toward one another to open the central orifice 275 sufficiently to allow the proximal end 109 of the endotracheal tube 100 to fit through the enlarged central orifice 275. The faceplate 200 is moved downward to the selected depth localizer recess 111, and the two overlapping faceplate sections 230 and 231 are moved away from one another to constrict the central orifice 275 around the selected recess 111. The fixation bands 430 and 431, which are attached to the posterior portion 400 of the stabilization collar 500, are passed forward through the slots 250 and 251 of the faceplate sections 210 and 211 and are looped back on themselves to attach with conventional hook and loop connections. The tautness or tension in the fixation bands 430 and 431 holds the faceplate 200 in position over the patient's mouth 51 while simultaneously constricting the central orifice 275 within the selected recess 111 to restrain the endotracheal tube 100 relative to the faceplate 200 at the appropriate depth of insertion within the patient's trachea 54.

The described actions involved in using the airway stabilization system may be varied. For example, the posterior portion 400 of the stabilization collar 500 may be positioned behind the head and neck of the patient before the endotracheal tube 100 is inserted. After inserting the endotracheal tube, the anterior portion 300 of the stabilization collar 500 is connected to the posterior portion 400, the faceplate 200 is positioned and constricted around the endotracheal tube 100, and the faceplate 200 is fixed to the stabilization collar 500 with the fixation bands 430 and 431. Another alternative eliminates the use of the faceplate 200 by using umbilical tape to secure the endotracheal tube 100 in position. This is accomplished by tying the umbilical tape around the patient's head and affixing it to the patient's mouth. The remainder of umbilical tape is then tied securely around the endotracheal tube in one of the recesses 111. The umbilical tape does not need to be cinched down tightly around the endotracheal tube since movement of the tube 100 will be restricted when the tape tied in the selected recess encounters an annular flange 110. This ability to tie the umbilical tape around the endotracheal tube 100 without the requirement of cinching it down tightly prevents the restriction in cross-sectional size of the endotracheal tube that is common when the umbilical tape is tightly cinched against the tube to attempt to prevent movement. The umbilical tape may also be used in this manner by attaching it to the stabilization collar 500 rather than around the head of the patient. A further alternative involves connecting the faceplate sections 210 and 211 relative to the face of the patient with adhesive tape A major advantage of the airway stabilization system is that it inhibits movement of the endotracheal tube 100 by the retention between the faceplate 200 and the selected recess 111 between the flanges 110, by the taut affixation of the faceplate 200 to the stabilization collar 500 through the fixation bands 430 and 431, and by the immobilization from the stabilization collar 500 to prevent flexion and extension the head 56 and neck 55. Consequently, the endotracheal tube 100 is maintained in a proper position for intubation despite moving the patient and inadvertent movement of ventilation equipment that may be attached to the endotracheal tube 100.

If necessary, a suction catheter may be placed through the lateral openings 240 and 241 of the faceplate sections 210 and 211 and into the patient's mouth 51 to suction fluids out of the patient's oral cavity (FIGS. 1 and 2). If the patient begins to bite down on the endotracheal tube, a conventional oralpharyngeal airway (OPA) can be placed through one of lateral openings 240 and 241 to act as a bite-block. Consequently, a bite-block need not be incorporated as a necessary or integral part of the faceplate 200. Instead, a bite-block may be used only when necessary and omitted when not needed.

Any necessary oral care can be administered through the lateral openings 240 and 241. Visualization of the oral cavity is facilitated by making the faceplate sections 210 and 211 from clear plastic. The adjustability provided by the fixation bands 430 and 431 allows the faceplate 200 to be adjusted in position on the face of the patient to minimize the possibility of pressure sores and to facilitate oral care. Incorporating the stripe 106 of radio-opaque material along the length of the endotracheal tube 100 allows the endotracheal tube to be located radiographically relative to anatomic structures by a chest x-ray.

Many other advantages and improvements will be apparent upon gaining a full understanding and appreciation of the various aspects of the complete airway stabilization system. Presently preferred embodiments of the invention and many of its improvements have been described with a degree of particularity. This description is a preferred example of implementing the invention, and is not necessarily intended to limit the scope of the invention. The scope of the invention is defined by the following claims.

The invention claimed:

1. A stabilization system for maintaining an airway in a patient requiring an endotracheal tube, the patient having a head, a face, a mouth, an oral cavity, a trachea, vocal cords, a neck, a chest and a chin, the system comprising:

a retention structure secured to the endotracheal tube;

a restraining device adapted to be secured to the patient, the restraining device being structured and arranged to releasably engage the retention structure and to cooperate therewith to prevent movement of the endotracheal tube, the restraining device including a pair of slidable overlapping faceplate sections operatively connected to one another and adapted to be positioned over the mouth of the patient, each of the overlapping faceplate sections including a lateral opening of a predetermined configuration, the lateral openings overlapping one another to form a central orifice in the restraining device structured and arranged to receive the endotracheal tube, wherein the central orifice is expandable and contractible in response to the movement of the overlapping faceplate sections, one of the faceplate sections having a plurality of channels adjacent the central orifice, each of the channels being a narrow and elongated aperture through the faceplate section, and the other faceplate section having a plurality of protrusions, each protrusion being slidably disposed in a corresponding one of the channels, the protrusion protruding through the channel to extend beyond the channel; and a fixation structure operatively connected to the restraining device and adapted to extend behind the patient's head and to hold the restraining device in place.

2. The stabilization system of claim 1 wherein the endotracheal tube has an exterior dimension and wherein the retention structure comprises at least one annular flange having an exterior dimension which is greater than the exterior dimension of the endotracheal tube.

3. The stabilization system of claim 2 wherein the retention structure further includes at least one structural recess disposed adjacent to the at least one annular flange.

4. The stabilization system of claim 3 wherein the restraining device is structured and arranged to releasably engage the at least one structural recess and the at least one adjacent annular flange to prevent movement of the endotracheal tube.

5. The stabilization system of claim 3 wherein the central orifice operatively receives the at least one structural recess and is in operative contact with the at least one adjacent annular flange to prevent movement of the endotracheal tube.

6. The stabilization system of claim 1 wherein the fixation structure comprises at least one fixation band operatively connected to each of the overlapping faceplate sections and extending behind the head of the patient.

7. The stabilization system of claim 6 wherein the at least one fixation band is structured and arranged to maintain the central orifice in operative contact with the at least one structural recess and the at least one adjacent annular flange to prevent movement of the endotracheal tube.

8. The stabilization system of claim 6 wherein each of the at least one fixation bands is selectively adjustable to fit the patient's head.

9. The stabilization system of claim 1 wherein the retention structure is integrally formed with the endotracheal tube.

10. The stabilization system of claim 6 wherein each the at least one fixation bands is structured and arranged to maintain the restraining device in a preselected position on the patient's face.

11. The stabilization system of claim 1, wherein spreading the overlapping faceplates in opposing directions contracts the central orifice.

12. The stabilization system of claim 1, wherein the lateral opening of one of the faceplate sections is disposed between the channels and the lateral opening of the other faceplate section is disposed between the protrusions.

* * * * *